United States Patent [19]

Moran et al.

[11] Patent Number: 4,875,780
[45] Date of Patent: Oct. 24, 1989

[54] METHOD AND APPARATUS FOR INSPECTING RETICLES

[75] Inventors: Kevin E. Moran, Belmont; Michael L. Smith, Matthews; Ernest R. Lippard, III, Charlotte, all of N.C.

[73] Assignee: Eastman Kodak Company, Rochester, N.Y.

[21] Appl. No.: 160,194

[22] Filed: Feb. 25, 1988

[51] Int. Cl.⁴ .............................................. G01N 21/47
[52] U.S. Cl. ..................................... 356/446; 356/237
[58] Field of Search .......................... 356/445, 446, 237

[56] References Cited

U.S. PATENT DOCUMENTS 3,125,265 3/1964 Warren et al.
3,836,261 9/1974 Clarke ................................. 356/237
3,992,111 11/1976 Roulier et al.
4,184,082 1/1980 Peoples.
4,376,583 3/1983 Alford et al. ........................ 356/237
4,614,427 9/1986 Koizumi et al. ..................... 356/237
4,630,276 12/1986 Moran .................................. 356/237
4,669,875 6/1987 Shiba et al. ......................... 356/237

Primary Examiner—Vincent P. McGraw
Assistant Examiner—S. A. Turner
Attorney, Agent, or Firm—Bell, Seltzer, Park & Gibson

[57] ABSTRACT

A laser light inspection device for inspecting opposite surfaces of a workpiece with a low angle laser light beam. The laser light beam is directed in successive scans of a first and second sides in a repetitive manner using a pair of dividing mirrors and a pair of low angle mirrors. Light reflected by any debris back toward the direction of origin of the light beam is collected and analyzed.

46 Claims, 1 Drawing Sheet

METHOD AND APPARATUS FOR INSPECTING RETICLES

FIELD OF THE INVENTION

This invention relates to a laser scanning system for inspecting opposite surfaces of a flat workpiece and more particularly a low incident angle laser scanning system for inspecting opposite surfaces of a reticle mask to be used in the production of silicon microchips.

BACKGROUND OF THE INVENTION

In the process of manufacturing silicon microchips, light is directed through a reticle mask to etch circuits into a silicon wafer disk. The presence of dirt, dust, smudges or other foreign matter on the surfaces of the reticle mask or the silicon water is highly undesirable and adversely affects the resulting circuits. As a result, the reticles and silicon wafers are necessarily inspected before use. One common inspection technique is for a human inspector to visually examine each surface under intense light and magnification. However, debris that is smaller than can be visually detected impairs the resulting microchips.

Laser surface inspection devices have been developed for inspecting the surface of silicon wafers to accurately detect small particles. Examples of such devices are disclosed in Alford et al U.S. Pat. No. 4,376,583 issued Mar. 15, 1983, and Moran U.S. Pat. No. 4,630,276 issued Dec. 16, 1986. In these known laser surface inspection systems, a laser beam is traversed across the surface of the silicon wafer and the reflections from the wafer are collected and analyzed to provide information about any debris present on the wafer surface. In the absence of debris, all of the light is specularly reflected from the surface. In locations where the beam strikes surface debris, the light is scattered. By separately collecting the scattered and specularly reflected light, the inspection device can accurately determine the surface conditions of silicon wafer disks.

However, such devices are not suitable for inspecting a reticle. The reticle has an extremely thin coating on the surface to form the masking. The edges of the coating tend to scatter light which causes spurious detections of foreign matter. The complexity of the circuits would cause the inspection device to determine that an otherwise clean reticle is saturated with debris. The use of such prior art devices is further unsuitable because only one side of the workpiece is inspected. Both sides of a reticle must be clean and therefore both sides need to be inspected.

SUMMARY OF THE INVENTION

In the present invention the aforementioned problems are solved by the provision of a laser inspection system that continuously and substantially simultaneously scans both sides of the reticle to detect surface contamination. The laser light beam is scanned across both surfaces at a relatively low angle so that the light scattered by the edge of the mask coating is minimized and only surface debris or contamination is detected. Inspecting both sides of the reticle at the same time minimizes handling, reduces the risk of subsequent contamination and minimizes the time required for inspection.

The laser scanning system in accordance with the present invention comprises a means for transporting a workpiece along a material path, a means for generating a laser light beam, a means for repeatedly scanning the laser light beam along a predetermined scan path, and means in the scan path for dividing the laser light beam into a first sweeping inspection scan oriented toward one side of the material path and a second sweeping inspection scan oriented toward the opposite side of the material path. The laser scanning system further comprises means to direct said first and second sweeping inspection scans at a low angle of incidence to the material path and collecting means adjacent the opposite sides the material path for collecting light reflected from the material path.

Additionally the system may be provided with a timing sensor and electronic control and analysis means to accurately locate and resolve any debris on the surfaces. The system may also be provided with an optical cell for forming the laser scan into a collimated, substantially parallel scan pattern.

BRIEF DESCRIPTION OF THE DRAWINGS

Some of the aspects of the invention having been stated, others will appear as the description proceeds when taken in connection with the accompanying drawings, in which.

DETAILED DESCRIPTION OF THE INVENTION

Figure 1:
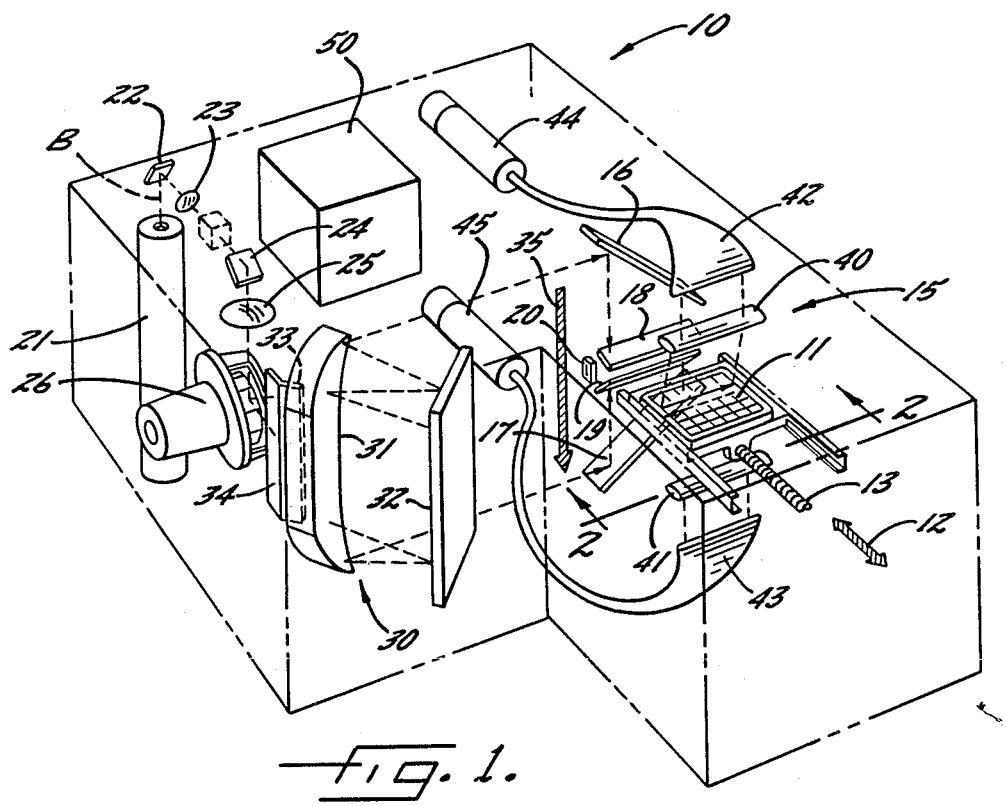
FIG. 1 is a schematic perspective view of the reticle inspection system.

With reference to FIG. 1, the reticle inspection system is generally indicated at 10. The system is preferably enclosed by a housing (shown in broken lines) and comprises a laser light generating means 21 such as a low wattage helium neon laser for generating a laser light beam B. The beam B is focused by lenses 23 and 25 to form a narrow spot beam. Mirrors 22 and 24 turn the beam B and direct it to a rotating polygonal mirror 26. The rotating mirror 26 causes the laser beam to repeatedly scan at high speed. The scanning laser beam is directed by a bounce mirror 33 to an optical cell generally indicated at 30 which includes a curved mirror 31 and a planar mirror 32. The curved mirror 31 and planar mirror are shaped and positioned so that the scanning laser light beam is reflected between each mirror a plurality of times before emerging from the cell. As a result of the consecutive reflections, the optical cell 30 converts the essentially radiating laser scan into a collimated, substantially parallel scan pattern The optical cell is discussed in Moran U.S. Pat. No. 4,630,276 which is incorporated by reference herein. In the illustrated embodiment, the rotating mirror 26 along with the optical cell 30 and the bounce mirrors 33 and 34 comprise a scan generating means.

The laser scan upon emerging from the optical cell is directed by a bounce mirror 34 to a scanning head, generally indicated at 15. At the scanning head, the laser beam moves along a predetermined scan path as indicated by the downwardly pointing arrow 35. Each successive scan begins at the top of the scan path and moves downwardly. At each point during the scan, the laser beam remains oriented substantially parallel to the orientation of the beam at each other point during the scan. The scanning head 15 comprises a pair of generally perpendicular dividing mirrors 16 and 17 which are positioned on opposite sides of a material path 12 and approximately 45° thereto. The laser scan path is effectively divided by the dividing mirrors 16 and 17 such that during the upper portion of the scan path the beam is intercepted by the first dividing mirror 16 and forms a first sweeping inspection scan while during the lower portion of the scan path the beam is intercepted by the second dividing mirror 17 and forms a second sweeping inspection scan. The first sweeping inspection scan is oriented toward one side of the material path 12 and the second sweeping inspection scan toward the opposite side in a generally perpendicularly manner. A pair of low angle mirrors 18 and 19 are positioned on opposite sides of the material path, with the reflective surface directed away from the path and toward a respective one of the pair of dividing mirrors. Low angle mirror 18 receives the first sweeping inspection scan from dividing mirror 16 and reflects it at low angle to the surface of the workpiece 11. Similarly, low angle mirror 19 receives the second sweeping inspection scan and directs it towards the opposite side of workpiece 11. The low angle minimizes the light scattered by the mask coating on the reticle and is generally in the range of about 2° to about 10°, but preferably about 5°. The sweeping inspection scans define respective linear strike paths 48 and 49 on opposite surfaces of the workpiece as the scans sweep transversely across the workpiece. A suitable workpiece transport means 13, such as a conveyor or robotic arm, is provided on the material path for moving the workpiece past the strike paths so that each entire surface is scanned. It will thus be seen that during each downward sweep or scan of the laser beam along scan path 35, the laser inspection beam is caused to pass successively across the upper and lower surfaces of a workpiece positioned at the strike paths 48, 49.

Figure 3:
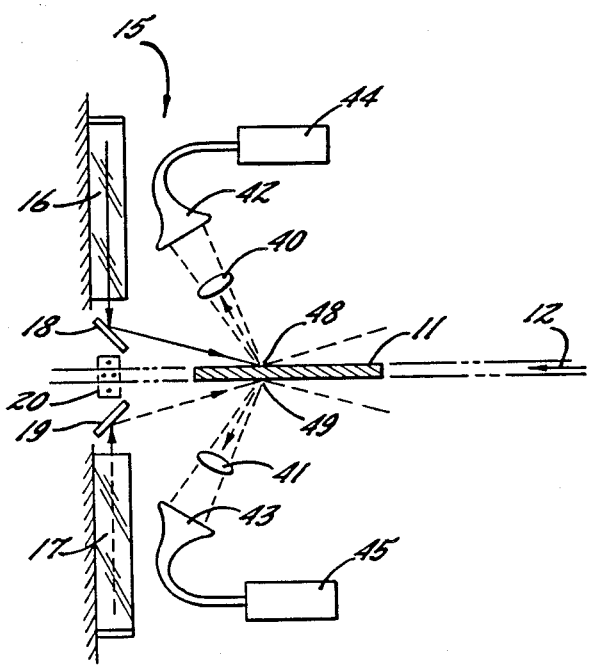
FIG. 3 is a schematic side view of the inspection head taken substantially along the line 3—3 in FIG. 2.

The inspection of the surfaces is accomplished by collecting reflected light and analyzing it. In the preferred embodiment illustrated herein, only scattered light is collected, but it is understood that in certain instances it may be desirable to additionally collect specularly reflected light. The collecting means comprises lenses 40 and 41, fiber optic strands 42 and 43, and photodetectors 44 and 45 such as photomultiplier tubes. The lenses 40 and 41 collect light which is reflected from the surface and focus the reflected light into the ends of the fiber optic strands 42 and 43 which transmit the collected light to the photodetectors 44 and 45. The photodetectors 44 and 45 convert the light into electrical signals for the electronic control and analysis means 50. The reflected light indicates the presence of foreign matter or dirt on the surface and the intensity of the reflected light indicates the size of the dirt particle. As such, the electrical signals indicate the size of the dirt particles present. The electronic control and analysis means 50 includes a microprocessor programmed for processing the data received from the photomultiplier tubes to determine the surface condition of the workpiece. The positioning of the collecting means assists the inspection system in ignoring the masking layer on the surface of the reticle. The masking layer on the reticle is extremely thin (approximately 1,000 to 2,000 angstroms), and therefore reflects a neglible amount of light back towards the source of a low angle light beam. As such, the collecting lenses 40, 41 are located between the low angle mirrors 18 and 19 and the strike paths 48 and 49 as shown best in FIG. 3.

A timing sensor 20 is provided in the scan path to sense the instant the laser beam crosses the position of the sensor. The sensor 20 may comprise one or more photoelectric cells or light responsive electronic devices. The timing sensor 20 is preferably located at a point on the scan path between the lowermost portion of the upper dividing mirror 16 and the uppermost portion of the lower dividing mirror since this portion of the scan path is dead space, with no light being directed to either surface of the workpiece. However, the timing sensor 20 may be optionally provided at one end of the scan path. The electronic control and analysis means 50 uses the timing data to help interpret the reflected light data. For example, the timing signals provide the electronic control and analysis means 50 with the necessary information in conjunction with the reflected light data to locate the particles on the surface. The control and analysis means 50 keeps track of the number, location and sizes of the dirt particles for a subsequent decision to pass or fail the reticle. The timing sensor 20 can also be arranged to provide other information to the electronic control and analysis mean 50 such as the focus, the intensity and the alignment of the beam, etc.

Figure 2:
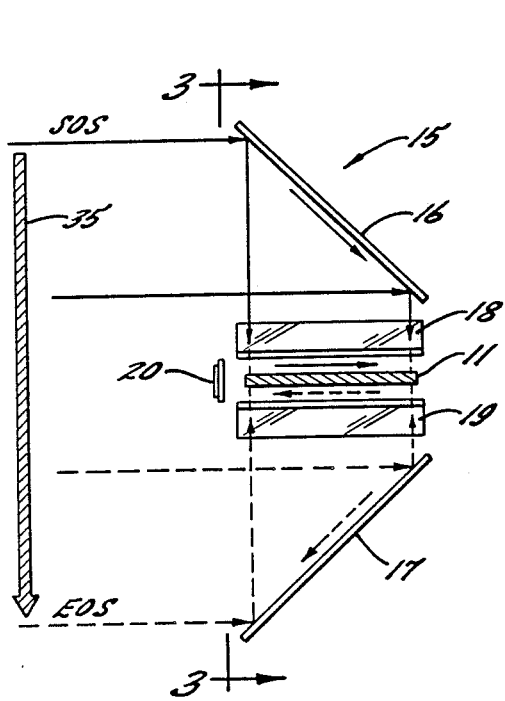
FIG. 2 is a schematic end view of the inspection head taken substantially along the line 2—2 in FIG. 1.

In operation, as shown in FIG. 2, at the Start of Scan (SOS) the laser beam (shown in dark line) is received by the upper extended portion of the top dividing mirror 16. The laser beam is reflected down onto the top low angle mirror 18 which directs the laser beam at a low angle of incidence to the left edge of workpiece 11. As the laser beam moves across the laser scan path, the beam traverses across the reflective surfaces of mirror 16 and mirror 18 and across the top surface of workpiece 11. When the scan reaches the lower portion of mirror 16, the laser beam is directed onto the right edge of the top surface of the workpiece 11, and the top surface has completed one sweep of the inspection scan. The laser scan continues through a dead space between the lower portion of the upper dividing mirror 16 and the upper portion of lower dividing mirror 17. When the laser beam reaches the upper portion of the lower dividing mirror 17, the laser beam (now shown in broken lines) is directed to the low angle mirror 19 positioned below the material path 12, and reflected to the lower right edge of workpiece 11. As the scan progresses down the lower dividing mirror 17 the laser beam moves across the workpiece until it reaches the left edge of the workpiece 11. This is the end of the scan (EOS) and both sides of the reticle have had one sweep of the inspection scan. As the reticle is moved along the material path, the laser continuously scans across the surfaces, forming a series of adjacent parallel scans. Reflected light is continuously collected by said collecting means and the data therefrom is interpreted by the electronic control and analysis means 50.

In the drawings and specification, there has been set forth a preferred embodiment of the invention, and although specific terms are employed, they are used in a generic and descriptive sense only and not for purposes of limitation.

We claim:

1. A laser scanning system for inspecting opposite surfaces of a workpiece, said system comprising means for transporting a workpiece along a material path, laser light generating means for generating a laser light beam, scan generating means arranged to receive said laser light beam and to repeatedly scan the laser light beam along a predetermined scan path, a timing sensor positioned in said scan path to sense the laser light beam crossing the position of said timing sensor, means positioned in said scan path for receiving said laser light beam and for dividing said laser light beam into a first sweeping inspection scan oriented toward one side of said material path and a second sweeping inspection scan oriented toward the opposite side of said material path, means arranged to receive each of said first and second sweeping inspection scans and to direct the same at a low angle of incidence to said material path, and means arranged adjacent said opposite sides of said material path for collecting light reflected from a workpiece in said material path.

2. The system according to claim 1, wherein said dividing means comprises a pair of mirrors positioned on opposite sides of the material path, generally perpendicular to each other and about 45° to the material path, and such that the scan path traverses first across one of said pair of mirrors and then across the second of said pair of mirrors.

3. The system according to claim 1, wherein said dividing means comprise a pair of mirrors positioned on opposite sides of said material path, and wherein said low angle directing means comprise a pair of mirrors positioned on opposite sides of said material path with the reflective surface facing generally away from the material path and toward a respective one of said dividing mirrors for receiving the scan therefrom and directing the scan at a low angle onto said material path.

4. The system according to claim 1, wherein said timing sensor is positioned generally at the center of said scan path and adjacent said material path, said timing sensor comprises at least one photoelectric cell.

5. The system according to claim 1, further comprising electronic control and analysis means connected to said collecting means for processing the data received therefrom.

6. The system according to claim 1, wherein said low angle directing means are so oriented that said first sweeping inspection scan intersects with said one side of said material path to form a first strike path, and said second sweeping inspection scan intersects with said opposite side of said material path to form a second strike path, further wherein said collecting means is positioned on opposite sides of said workpiece generally between said directing means and said strike paths.

7. The system according to claim 6 wherein said collecting means includes lenses positioned for collecting light reflected from a workpiece in said material path, fiber optic strands cooperating with said lenses for receiving the light from said lens, and photodetectors connected to said fiber optic strands for receiving light from said fiber optic strands.

8. The system according to claim 7, wherein said photodetectors convert the collected light to an electrical signal indicative of the intensity of the collected light, said system further including a timing sensor positioned in said scan path for sensing the laser light beam crossing the position of said timing sensor, and electronic control and analysis means for receiving and analyzing the data from the timing sensor and the photodetectors to record the number, size and locations of particles on the surface of a workpiece.

9. The system according to claim 1, wherein said scan generating means includes means for moving the laser light beam along said predetermined scan path in a collimated, parallel scan pattern.

10. A laser scanning system for inspecting top and bottom surfaces of a horizontal workpiece, said system comprising means for transporting a workpiece along a horizontal material path, laser light generating means for generating a laser light beam, scan generating means including a folded optical cell arranged to receive said laser light beam and to repeatedly scan said laser light beam along a predetermined scan path in a collimated, parallel scan pattern, a pair of mirrors positioned in said scan path between the optical cell and the material path for receiving said laser light beam and for dividing said laser light beam into a first sweeping inspection scan oriented toward one side of said material path and a second sweeping inspection scan oriented toward the opposite side of said material path, means arranged to receive each of said first and second sweeping inspection scans and to direct the same at a low angle of incidence to said material path, and means arranged adjacent said opposite sides of said material path for collecting light reflected from said material path.

11. The system according to claim 10, wherein said low angle directing means are so oriented that said first sweeping inspection scan intersects with said one side of said material path to form a first strike path and said second sweeping inspection scan intersects with said opposite side of said material path to form a second strike path, and wherein said collecting means is positioned on opposite sides of said workpiece generally between said directing means and said strike paths.

12. The system according to claim 11 wherein said collecting means includes lenses positioned for collecting light reflected from a workpiece in said material path, fiber optic strands cooperating with said lenses for receiving the light from said lens, and photodetectors connected to said fiber optic strands for receiving light from said fiber optic strands.

13. The system according to claim 12, wherein said photodetectors convert the collected light to an electrical signal indicative of the intensity of the collected light, said system further including a timing sensor positioned in said scan path for sensing the laser light beam crossing the position of said timing sensor, and electronic control and analysis means for receiving and analyzing the data from the timing sensor and the photodetectors to record the number, size and locations of particles on the surface of a workpiece.

14. The system according to claim 10 further including a timing sensor positioned on the scan path to sense the laser light beam crossing the position of the timing sensor.

15. The system according to claim 14, wherein said timing sensor is positioned generally at the center of said scan path and adjacent said material path, said timing sensor comprises at least one photoelectric cell.

16. The system according to claim 10, further comprising electronic control and analysis means connected to said collecting means for processing the data received therefrom.

17. A laser scanning system for inspecting top and bottom surfaces of a horizontal workpiece, said system comprising means for transporting a workpiece along a horizontal material path, a laser for generating a laser light beam, a rotating polygonal mirror positioned for receiving the laser light beam and to scan the laser light beam, a folded optical cell arranged to receive said scanning laser light beam and to form the scan into a collimated, parallel scan pattern and to direct it along a predetermined scan path, a pair of dividing mirrors positioned in said scan path on opposite sides of the material path generally perpendicular to each other and at approximately 45° to the material path to receive said laser light beam and divide said laser light beam into a first sweeping inspection scan oriented toward a first side of the material path and a second sweeping inspection scan oriented toward the opposite side of said material path, a pair of low angle mirrors arranged on opposite sides of the material path and between said pair of dividing mirrors on said scan path for receiving said first and second sweeping inspection scans and directing said first and second sweeping inspection scans at a low angle of incidence to said material path, collecting means including lenses arranged adjacent said opposite sides of said material path adjacent said pair of low angle mirrors for collecting light reflected from said material path, a timing sensor positioned in said scan path between said pair of low angle mirrors to sense the laser light beam crossing the position of the timing sensor, and electronic control and analysis means connected to said collecting means and said timing sensor for processing data received therefrom, wherein said laser beam traverses across a first of said pair of dividing mirrors and then across the second said pair of collecting means in a repeating manner.

18. The system according to claim 17, wherein said pair of low angle mirrors are so oriented that said first sweeping inspection scan intersects with said one side of said material path forms a first strike path and said second sweeping inspection scan intersects with said opposite side of said material path to form a second strike path, and wherein said collecting means is positioned on opposite sides of said workpiece generally between said directing means and said strike paths.

19. The system according to claim 17, wherein said collecting means further includes photodetectors for converting the collected light into electrical signals indicative of the intensity of the collected light, said electronic control and analysis means including means for recording the number, size and location of particles on the surfaces of the workpiece.

20. A method of scanning opposite sides of a workpiece as the workpiece moves along a material path, comprising the steps of generating a laser light beam, moving said laser light beam in a repetitive scan pattern along a predetermined scan path, directing the laser light beam during each scan into contact with a timing sensor positioned in the scan path, dividing the laser light scan pattern into first and second sweeping inspection scans and directing each of said first and second sweeping inspection scans toward first and second opposite sides of the workpiece at a low angle of incidence and collecting light reflected from the surface of said workpiece.

21. The method according to claim 20, wherein said step of collecting light further comprises collecting light that is reflected generally back towards the direction the light beam originated.

22. The method according to claim 20, wherein said step of dividing the laser light scan pattern is done by a pair of perpendicular dividing mirrors positioned on opposite sides of the workpiece and about 45° thereto.

23. The method according to claim 22, wherein said step of directing each of said first and second sweeping inspection scans at a low angle comprises directing the scans onto a pair of low angle mirrors positioned on opposite sides of the workpiece and facing generally away from the workpiece and toward a respective one of said dividing mirrors.

24. The method according to claim 20, further including the step of converting the collected light to an electrical signal indicative of the intensity of the light collected and analyzing the electrical signal to determine the size and number of particles on the surface.

25. The method according to claim 20, wherein the step of directing the laser light beam during each scan into contact with a timing sensor positioned in the scan path further includes the step of generating a timing signal to indicate to a control and analysis means the laser beam passing the position of the timing sensor so that positions of particles on the surfaces are precisely determinable.

26. The method according to claim 20, further including the step of analyzing the collected light by converting the collected light to an electrical signal indicative of the intensity of the collected light, generating a timing signal to indicate the laser beam passing a predetermined position, and accummulating the number, size and locations of particles on the surface of said workpiece.

27. A method of scanning opposite sides of a workpiece as the workpiece moves along a material path, comprising the steps of generating a laser light beam, scanning said laser light beam to generate a repetitive scan of laser light, reflecting the laser light scan between at least two mirrors a plurality of times to form a collimated, parallel scan pattern, dividing the laser light scan into a first and second sweeping inspection scans with a pair of perpendicularly arranged mirrors and reflecting each of said first and second sweeping inspection scans toward first and second opposite sides of the workpiece, reflecting each of said first and second laser scans at a low angle of incidence onto the workpiece with a second pair of mirrors disposed on said opposite sides of said workpiece and collecting light reflected from the surfaces of said workpiece.

28. The method according to claim 27, wherein said step of collecting light further comprises collecting light that is reflected generally back towards the direction the light beam originated.

29. The method according to claim 27, wherein said step of dividing the laser light scan pattern is done by a pair of perpendicular dividing mirrors positioned on opposite sides of the workpiece and about 45° thereto.

30. The method according to claim 29, wherein said step of directing each of said first and second sweeping inspection scans at a low angle comprises directing the scans onto a pair of low angle mirrors positioned on opposite sides of the workpiece and facing generally away from the workpiece and toward a respective one of said dividing mirrors.

31. The method according to claim 27, further including the step of converting the collected light to an electrical signal indicative of the intensity of the light collected and analyzing the electrical signal to determine the size and number of particles on the surface.

32. The method according to claim 27, further including the step of directing the laser light beam during each scan into contact with a timing sensor positioned in the scan path to generate a timing signal to indicate to a control and analysis means the laser beam passing the position of the timing sensor so that positions of particles on the surfaces are precisely determinable.

33. The method according to claim 27, further including the step of analyzing the collected light by converting the collected light to an electrical signal indicative of the intensity of the collected light, generating a timing signal to precisely indicate the instant that the laser beam passes a predetermined position, and accummulating the number, size and locations of particles on the surface of said workpiece.

34. A laser scanning system for inspecting opposite surfaces of a workpiece, said system comprising means for transporting a workpiece along a material path, laser light generating means for generating a laser light beam, scan generating means arranged to receive said laser light beam and to repeatedly scan the laser light beam along a predetermined scan path, said scan generating means including means for moving said laser light beam along said predetermined scan path in a collimated, generally parallel scan pattern, means positioned in said scan path for receiving said laser light beam and for dividing said laser light beam into a first sweeping inspection scan oriented toward one side of said material path and a second sweeping inspection scan oriented toward the opposite side of said material path, means arranged to receive each of said first and second sweeping inspection scans and to direct the same at a low angle of incidence to said material path, and means arranged adjacent said opposite sides of said material path for collecting light reflected from a workpiece in said material path.

35. The system according to claim 34, wherein said dividing means comprises a pair of mirrors positioned on opposite sides of the material path, generally perpendicular to each other and about 45° to the material path, and such that the scan path traverses first across one of said pair of mirrors and then across the second of said pair of mirrors.

36. The system according to claim 34, wherein said dividing means comprise a pair of mirrors positioned on opposite sides of said material path, and wherein said low angle directing means comprise a pair of mirrors positioned on opposite sides of said material path with the reflective surface facing generally away from the material path and toward a respective one of said dividing mirrors for receiving the scan therefrom and directing the scan at a low angle onto said material path.

37. The system according to claim 34 further including a timing sensor positioned generally in the center of the scan path adjacent said material path to sense the laser light beam crossing the position of the timing sensor.

38. The system according to claim 34, wherein said low angle directing means are so oriented that said first sweeping inspection scan intersects with said one side of said material path to form a first strike path, and said second sweeping inspection scan intersects with said opposite side of said material path to form a second strike path, further wherein said collecting means is positioned on opposite sides of said workpiece generally between said directing means and said strike paths.

39. The system according to claim 35, wherein said collecting means includes lenses positioned for collecting light reflected from a workpiece in said material path, fiber optic strands cooperating with said lenses for receiving the light from said lens, and photodetectors connected to said fiber optic strands for receiving light from said fiber optic strands.

40. The system according to claim 39, wherein said photodetectors convert the collected light to an electrical signal indicative of the intensity of the collected light, said system further including a timing sensor positioned in said scan path for sensing the laser light beam crossing the position of said timing sensor, and electronic control and analysis means for receiving and analyzing the data from the timing sensor and the photodetectors to record the number, size and locations of particles on the surface of a workpiece.

41. A method of scanning opposite sides of a workpiece as the workpiece moves along a material path, comprising the steps of generating a laser light beam, moving said laser light beam in a repetitive collimated, generally parallel scan pattern along a predetermined scan path, dividing the laser light scan pattern into first and second sweeping inspection scans and directing each of said first and second sweeping inspection scans toward first and second opposite sides of the workpiece at a low angle of incidence and collecting light reflecting from the surface of said workpiece.

42. The method according to claim 41, wherein said step of collecting light further comprises collecting light that is reflected generally back towards the direction the light beam originated.

43. The method according to claim 41, wherein said step of dividing the laser light scan pattern is done by a pair of perpendicular dividing mirrors positioned on opposite sides of the workpiece and about 45° thereto, and wherein said step of directing each of said first and second sweeping inspection scans at a low angle comprises directing the scans onto a pair of low angle mirrors positioned on opposite sides of the workpiece and facing generally away from the workpiece and toward a respective one of said dividing mirrors.

44. The method according to claim 41, further including the step of converting the collected light to an electrical signal indicative of the intensity of the light collected and analyzing the electrical signal to determine the size and number of particles on the surface.

45. The method according to claim 41, further including the step of directing the laser light beam during each scan into contact with a timing sensor positioned in the scan path to generate a timing signal to indicate to a control and analysis means the laser beam passing the position of the timing sensor so that positions of particles on the surfaces are precisely determinable.

46. The method according to claim 41, further including the step of analyzing the collected light by converting the collected light to an electrical signal indicative of the intensity of the collected light, generating a timing signal to indicate the laser beam passing a predetermined position, and accumulating the number, size and locations of particles on the surface of said workpiece.

* * * * *

UNITED STATES PATENT AND TRADEMARK OFFICE
CERTIFICATE OF CORRECTION

PATENT NO. : 4,875,780

DATED : October 24, 1989

INVENTOR(S) : Kevin E. Moran, et al.

It is certified that error appears in the above-identified patent and that said Letters Patent is hereby corrected as shown below:

Column 1, line 17, "water" should be -- wafer --

Column 2, line 52, after "pattern" insert -- . --

Column 4, line 20, "mean" should be -- means --

Column 9, line 54, "35" should be -- 38 --

Signed and Sealed this

Seventh Day of May, 1991

Attest:

HARRY F. MANBECK, JR.

*Attesting Officer*  *Commissioner of Patents and Trademarks*